(12) United States Patent
Brown-Skrobot et al.

(10) Patent No.: US 7,879,288 B2
(45) Date of Patent: Feb. 1, 2011

(54) METHOD AND APPARATUS OF STERILIZATION USING MONOCHROMATIC UV RADIATION SOURCE

(75) Inventors: Susan K. Brown-Skrobot, Jacksonville, FL (US); James A. Ebel, Jacksonville, FL (US); John B. Enns, Jacksonville, FL (US); Gregory A. Hill, Ponte Vedra Beach, FL (US); Allan W. Kimble, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 10/939,818

(22) Filed: Sep. 13, 2004

(65) Prior Publication Data

US 2005/0079096 A1   Apr. 14, 2005

Related U.S. Application Data

(63) Continuation of application No. 09/947,873, filed on Sep. 6, 2001, now abandoned, which is a continuation-in-part of application No. 09/259,758, filed on Mar. 1, 1999, now abandoned.

(51) Int. Cl.
| | |
|---|---|
| A61L 2/00 | (2006.01) |
| A62B 7/08 | (2006.01) |
| A24F 15/00 | (2006.01) |
| B01J 19/00 | (2006.01) |
| B01J 19/08 | (2006.01) |
| B65D 85/04 | (2006.01) |
| B65D 83/10 | (2006.01) |
| G01N 23/00 | (2006.01) |

(52) U.S. Cl. ............................... 422/22; 422/1; 422/24; 422/40; 422/58; 422/121; 422/123; 422/186; 250/455.11; 206/51; 206/270; 206/363

(58) Field of Classification Search ............ 422/1, 422/22, 24, 40, 58, 121, 123, 186; 250/455.11; 206/363, 51, 270
See application file for complete search history.

(56) References Cited

U.S. PATENT DOCUMENTS 3,753,651 A   8/1973 Boucher
(Continued)

FOREIGN PATENT DOCUMENTS

CN   2206118 Y   8/1995
(Continued)

OTHER PUBLICATIONS

Singleton, P. et al., "Dictionary of Microbiology and Molecular Biology", John Wiley & Sons, New York, NY, pp. 702-703.
(Continued)

*Primary Examiner*—Jill Warden
*Assistant Examiner*—Monzer R Chorbaji

(57) ABSTRACT

This invention provides a process of sterilizing a medical device, and preferably the contents of a sealed container which comprises said medical device, comprising the step of exposing said medical device to monochromatic ultraviolet radiation whereby the $D_{value}$ of *Bacillus stearothermophilus* (ATCC 7953) is at least 23.7 mJ/cm² monochromatic ultraviolet radiation at 257 nm to the spore. Further, this invention provides a process of sterilizing a medical device comprising the step of subjecting said medical device to monochromatic ultraviolet radiation wherein the minimum total energy density of said monochromatic ultraviolet radiation at 257 nm which reaches the microorganisms present on said medical device is at least 284 mJ/cm².

This invention further provides an apparatus for delivering UV radiation to a medical device for sterilization comprising a laser and a scanner for the laser such that at least 284 mJ/cm² at 257 nm is applied to a treatment area for said medical device. This invention provides a process and apparatus in which sterilization can be achieved in less than 20 seconds, preferably less than 15 seconds, more preferably in less than 5 seconds. The process and apparatus are efficient and continuous.

15 Claims, 4 Drawing Sheets

U.S. PATENT DOCUMENTS

| | | | |
|---|---|---|---|
| 3,817,703 A * | 6/1974 | Atwood | 422/22 |
| 3,853,651 A | 12/1974 | Porte | |
| 3,941,670 A | 3/1976 | Pratt, Jr. | |
| 3,955,921 A | 5/1976 | Tensmeyer | |
| 4,042,325 A | 8/1977 | Tensmeyer | |
| 4,063,890 A * | 12/1977 | Baron | 422/24 |
| 4,304,895 A | 12/1981 | Loshaek | |
| 4,464,336 A | 8/1984 | Hiramoto | |
| 4,495,313 A | 1/1985 | Larsen | |
| 4,528,268 A | 7/1985 | Andersen | |
| 4,528,311 A | 7/1985 | Beard | |
| 4,565,348 A | 1/1986 | Larsen | |
| 4,629,896 A | 12/1986 | Bridgen | |
| 4,680,336 A | 7/1987 | Larsen | |
| 4,716,234 A | 12/1987 | Dunks | |
| 4,871,559 A | 10/1989 | Dun et al. | |
| 4,889,664 A | 12/1989 | Kindt-Larsen et al. | |
| 4,899,057 A * | 2/1990 | Koji | 250/436 |
| 4,910,942 A | 3/1990 | Dunn | |
| 5,034,235 A | 7/1991 | Dunn et al. | |
| 5,039,459 A | 8/1991 | Kindt-Larsen et al. | |
| 5,133,745 A | 7/1992 | Falcetta | |
| 5,196,458 A | 3/1993 | Nunez | |
| 5,232,367 A | 8/1993 | Vassiliadis et al. | |
| 5,252,484 A * | 10/1993 | Matner et al. | 435/287.4 |
| 5,256,751 A | 10/1993 | Vanderlaan | |
| 5,271,874 A | 12/1993 | Osipo | |
| 5,292,350 A | 3/1994 | Molock | |
| 5,304,584 A | 4/1994 | Nunez | |
| 5,311,223 A | 5/1994 | Vanderlaan | |
| 5,395,558 A | 3/1995 | Tsai | |
| 5,422,068 A * | 6/1995 | Shalaby et al. | 422/22 |
| 5,431,879 A | 7/1995 | Heyl | |
| 5,435,943 A | 7/1995 | Adams et al. | |
| 5,439,642 A * | 8/1995 | Hagmann et al. | 422/22 |
| 5,484,863 A | 1/1996 | Molok et al. | |
| 5,491,091 A | 2/1996 | Loshaek | |
| 5,618,492 A * | 4/1997 | Auten et al. | 422/22 |
| 5,648,402 A | 7/1997 | Nunez et al. | |
| 5,654,350 A | 8/1997 | Nunez et al. | |
| 5,681,871 A | 10/1997 | Molock | |
| 5,684,058 A | 11/1997 | Nunez et al. | |
| 5,688,475 A | 11/1997 | Duthie, Jr. | |
| 5,768,853 A | 6/1998 | Bushnell et al. | |
| 5,786,598 A * | 7/1998 | Clark et al. | 250/455.11 |
| 5,843,374 A | 12/1998 | Sizer | |
| 5,925,885 A | 7/1999 | Clark | |
| 6,244,707 B1 * | 6/2001 | Faubl | 351/160 H |
| 6,566,659 B1 | 5/2003 | Clark | |
| 6,592,816 B1 | 7/2003 | Ebel et al. | |
| 7,217,936 B2 | 5/2007 | Ressler | |
| 2005/0013729 A1 * | 1/2005 | Brown-Skrobot et al. | 422/24 |

FOREIGN PATENT DOCUMENTS

| | | |
|---|---|---|
| EP | 0222309 | 2/1990 |
| EP | 0479723 | 4/1992 |
| FR | 2 539 030 A1 * | 7/1984 |
| WO | 96/09775 | 4/1996 |
| WO | 97/35624 A1 | 10/1997 |
| WO | WO 97/35624 * | 10/1997 |
| WO | 97/43915 A1 | 11/1997 |

OTHER PUBLICATIONS

Warriner, K. et al., "Inactivation of *Bacillus subtilis* spores on packaging surfaces by u.v. excimer laser irradiation", Journal of Applied Microbiology, 2000, 88, 678-685.

European Search Report dated Jul. 5, 2000.

Singleton, P. et al., "Dictionary of Microbiology and Molecular Biology", John Wiley & Sons, New York, NY, pp. 702-703, Nov. 2006.

* cited by examiner

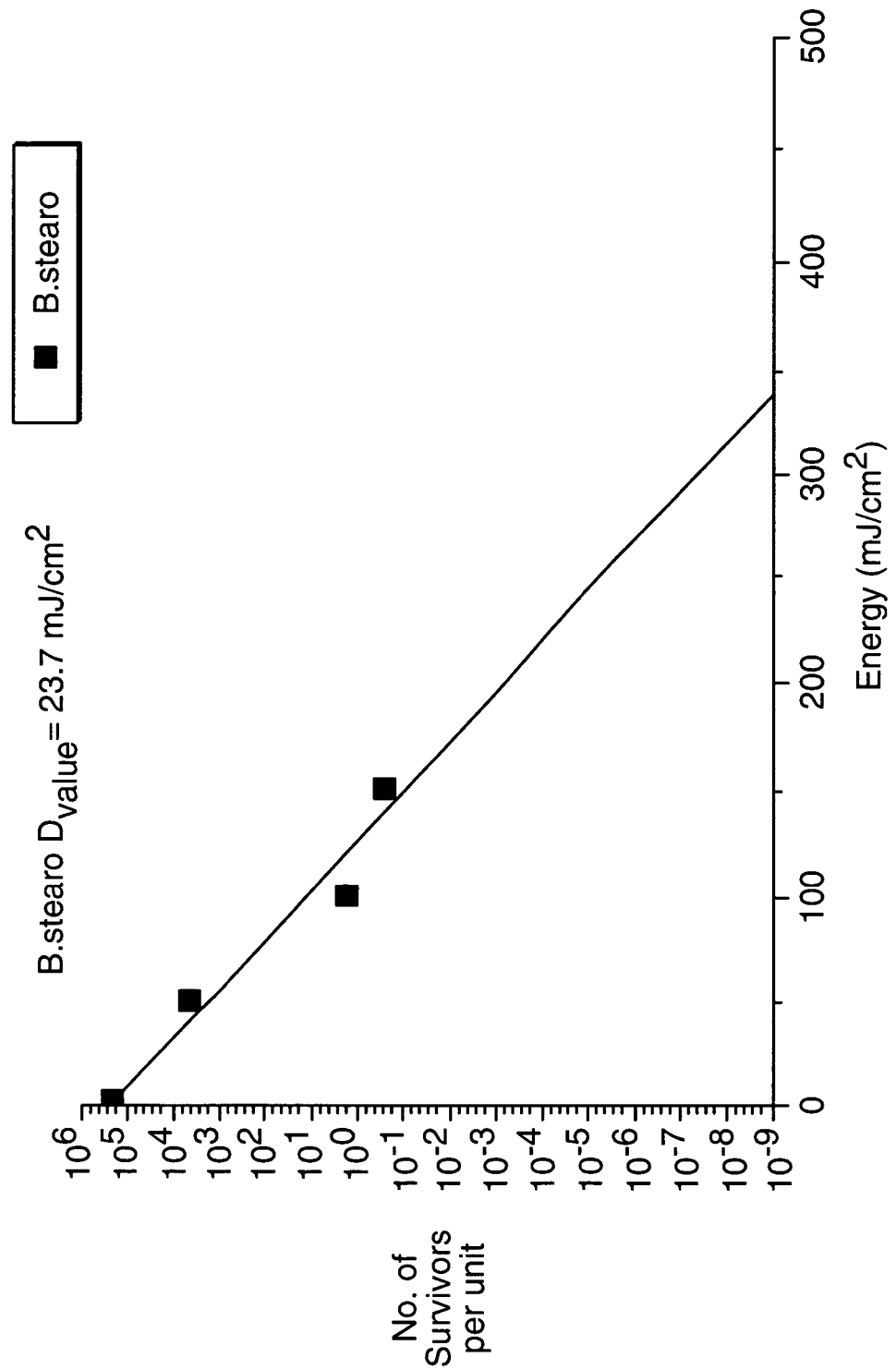

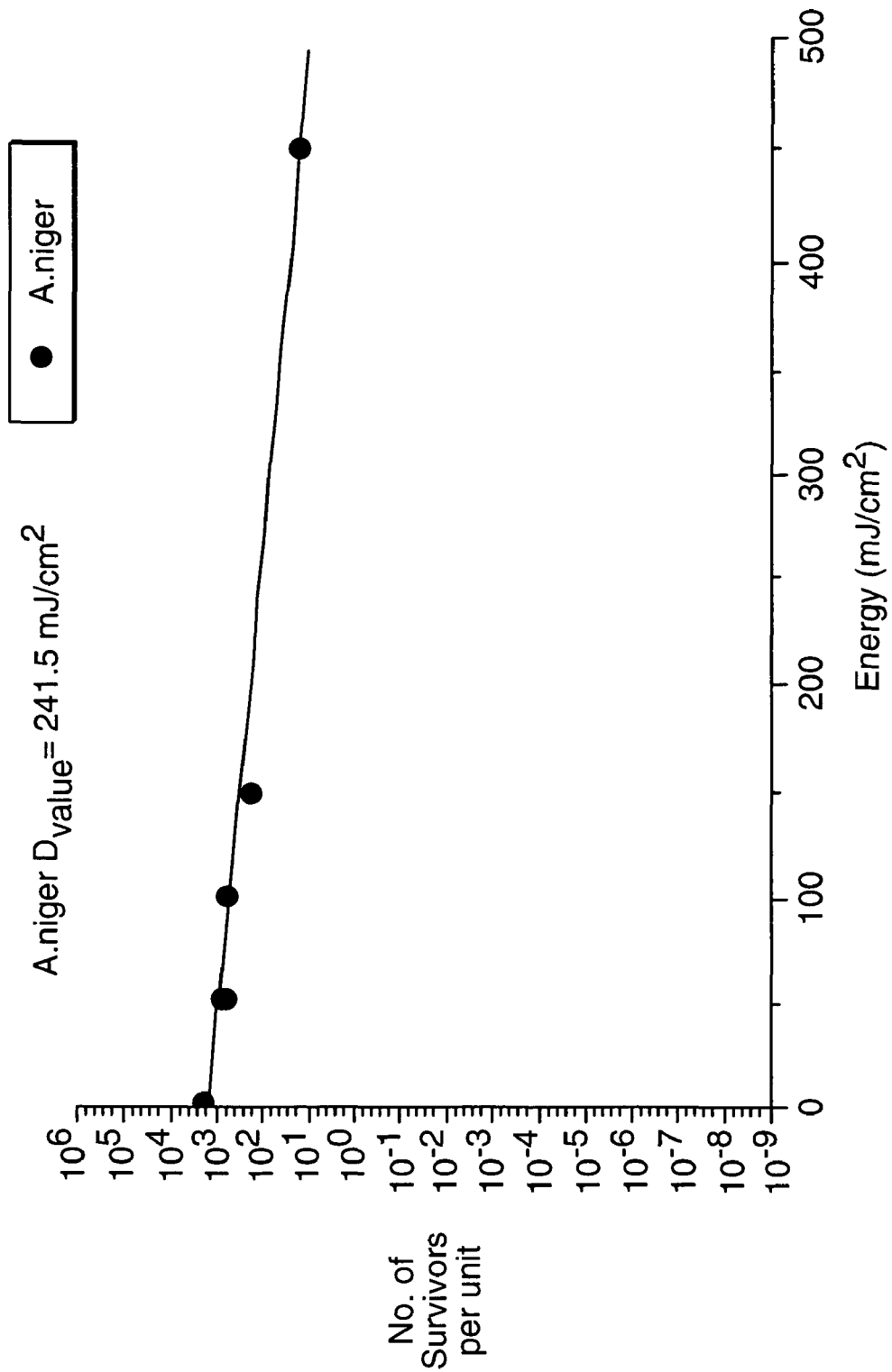

METHOD AND APPARATUS OF STERILIZATION USING MONOCHROMATIC UV RADIATION SOURCE

This application is a continuation of "Method and Apparatus of Sterilization Using Monochromatic UV Radiation Source", U.S. Ser. No. 09/947,873, filed Sep. 6, 2001 now abandoned (VTN-556 CIP), which is a continuation-in-part of a "Method Of Sterilization", U.S. Ser. No. 09/259,758, filed Mar. 1, 1999 now abandoned (VTN-388).

FIELD OF THE INVENTION

This invention relates broadly to sterilization of medical devices. More specifically, this invention relates to a novel process and apparatus for the sterilization of medical devices using monochromatic ultraviolet radiation from one or more monochromatic UV radiation sources.

DESCRIPTION OF THE RELATED ART

Medical device sterilization processes, and in particular commercial contact lens manufacturing sterilization processes, typically involve some form of temperature and/or pressure-based sterilization techniques. For example, a hydrophilic contact lens is typically first formed by injecting a monomer mixture into a mold. The monomer mixture is then polymerized (i.e. the lenses are cured). After other optional processing steps, such as quality inspections, the lens is placed into a container with a solution and the container is sealed. The packaged lens is sterilized by placing the container into an autoclave at an elevated temperature and pressure for an extended period of time, usually at least 15 minutes, typically 30 minutes. Although this commercial process produces thoroughly sterilized contact lenses, the batchwise autoclave sterilization step is time consuming and costly.

European Patent Application No. 0 222 309 A1 discloses a process using ozone in which packaging material is disinfected in a manufacturing setting. The process involves feeding an oxygen stream into an ozonating chamber, generating ozone from oxygen in the ozonating chamber, placing packaging containers in a sanitizing chamber, feeding the ozone into the sanitizing chamber, and purging the ozone from the sanitizing chamber with sterile air. The process requires that the ozone contact the packaging material for a predetermined time, followed by the sterile air purge step. The process is offered as an alternative to heat-steam sterilization, sterilization by application of electromagnetic radiation, or chemical agent sterilization.

U.S. Pat. No. 5,618,492 discloses a process for producing a sterile contact lens in a sealed container during a continuous production process wherein the contact lens is immersed in an ozone-containing solution within a container during a continuous lens packaging process, and the lens and container are subsequently subjected to monochromatic ultraviolet radiation primarily to degrade the ozone. This process sterilizes the contact lens and the container.

Non-ionizing radiation such as monochromatic ultraviolet (UV) light is known to damage the DNA of exposed cells. The UV radiation causes thymine to dimerize which inhibits replication of DNA during cell reproduction. UV radiation is used for disinfection in hospital rooms, nurseries, operating rooms and cafeterias. UV radiation is also used to sterilize vaccines, serum, toxins, municipal waste, and drinking waters. The major weakness of the efficacy of UV radiation as a sterilizer is that for most materials the radiation is not very penetrating, so the microorganisms to be killed must be directly exposed to the radiation.

A number of patents teach the application of UV radiation to disinfect and/or inactivate microorganisms to either reduce populations of microorganisms or to eliminate them.

U.S. Pat. No. 5,768,853 and WO96/09775 describe the use of a UV radiation producing apparatus which deactivates microorganisms in food.

U.S. Pat. No. 4,464,336 suggests a method of sterilization by using a flash discharge monochromatic ultraviolet lamp. The patent teaches that by applying short duration high intensity UV radiation that microorganisms will be destroyed; however, the conditions for sterilization are not disclosed, nor its application for medical devices.

U.S. Pat. No. 5,786,598 discloses the broad concept that a flash lamp system might be used for deactivating microorganisms in containers including a polyolefin container with a foil backing that contains a contact lens and a preservative fluid. Preservation is the use of physical and/or chemical means to kill or prevent the growth of those microorganisms which, by their growth and/or activities, may cause bio-deterioration of a given material or product. P. Singleton and D. Sainsbury, 1988. *Dictionary of Microbiology and Molecular Biology*, John Wiley & Sons, New York, N.Y., pp. 702-703. Although the patent discloses the idea of using a flash lamp system to sterilize contact lenses in a preserved solution in a container, there are no conditions defined to accomplish sterility, nor examples which show that sterility can be accomplished.

U.S. Pat. Nos. 5,034,235 and 4,871,559 disclose the use of intermittent pulses of very intense, very short duration pulses of light to inactivate microorganisms on the surface of food products, and suggests that the method can be used for packages, medical devices, and food products in packages.

A number of patents teach the use of lasers to sterilize and/or inactivate microorganisms to either reduce populations of microorganisms or to eliminate them.

U.S. Pat. No. 3,817,703 discloses the use of a high energy density pulsed laser of unspecified wavelength to sterilize wine.

U.S. Pat. No. 5,232,367 discloses the use of a high power pulsed Nd:YAG laser in dental applications to sterilize the bacteria in a tooth cavity and accessory canals.

U.S. Pat. No. 3,941,670 teaches the use of an infrared CW laser to alter the biological activity of molecular species, including sterilization.

U.S. Pat. Nos. 3,955,921 and 4,042,325 discuss the use of a pulsed laser to induce a plasma inside a container which sterilizes it.

A pulsed laser was used to inactivate *Bacillus subtilis* spores deposited on to planar aluminum and polyethylene packaging surfaces, K. Warriner, et al, "Inactivation of *Bacillus subtilis* spores on packaging surfaces by u.v. excimer laser irradiation," Journal of Applied Microbiology 2000, 88, 678-685.

There still remains a need for a time-efficient, continuous, effective sterilization process for pharmaceutical, medical, and cosmetic products which can be used in an inline mode in the manufacture of these products.

SUMMARY OF THE INVENTION

This invention provides a process of sterilizing a medical device, and preferably the contents of a sealed container which comprises said medical device, comprising the step of exposing said medical device to monochromatic ultraviolet radiation whereby the $D_{value}$ of *Bacillus stearothermophilus* (ATCC 7953) is at least 23.7 milliJoule per square centimeter (mJ/cm$^2$) for monochromatic ultraviolet radiation to the spore. Further, this invention provides a process of sterilizing a medical device comprising the step of subjecting said medical device to monochromatic ultraviolet radiation wherein the minimum total energy density of said monochromatic ultraviolet radiation which reaches the microorganisms present on said medical device is at least 25 mJ/cm$^2$.

This invention further provides an apparatus for delivering UV radiation to a medical device for sterilization. In one embodiment, the apparatus comprises at least one laser and preferably a scanner or set of optics such that the product can be exposed to the radiation. In an alternate embodiment the apparatus comprises the use of excimer lamps and suitable optical devices to concentrate the output of the lamps at the medical device.

The process and apparatus of the invention is used to provide sterilized medical devices. Further, this invention provides a process and apparatus in which sterilization can be achieved in less than 20 seconds, preferably less than 10 seconds, more preferably in less than 1 second. This invention provides a process and apparatus which sterilizes medical devices and optionally sterilizes the contents of the containers holding the medical devices. Preferably the process and apparatus can be incorporated into a manufacturing line. The process and apparatus are efficient and continuous.

DESCRIPTION OF THE FIGURES

The invention will be described with reference to the following figures:

FIG. 4 shows a graph used to determine the $D_{value}$ of *Bacillus stearothermophilus* (ATCC 7953).

FIG. 5 shows a graph used to determine the $D_{value}$ of *Aspergillis niger* (ATCC 16404).

DESCRIPTION OF THE INVENTION

Figure 1:
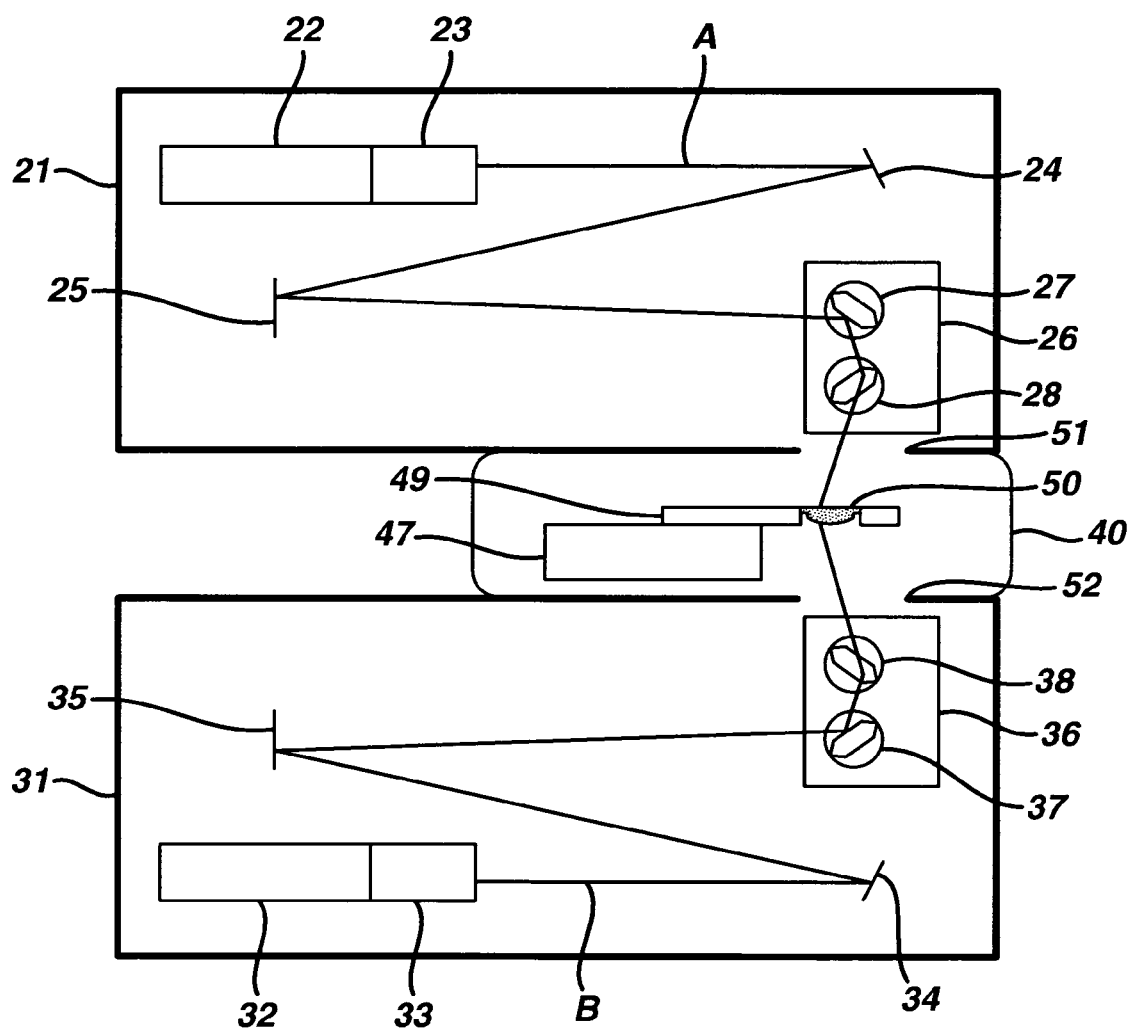
FIG. 1 illustrates one embodiment of an apparatus of this invention.

The term "sterile" or "sterilization" as used herein means the condition of an object, or an environment, which is free of all living cells, all viable spores (and other resistant and disseminative forms), and all viruses and subviral agents capable of replication. Sterility is assured by a minimum sterility assurance level (SAL) of $10^{-3}$, preferably $10^{-6}$, more preferably $10^{-9}$, and most preferably $10^{-12}$ when the container is inoculated with $10^6$ microorganisms. The minimum sterility assurance level is dependent on the type of medical device. For example, for sterilization of a single-use contact lens, the USFDA requires a minimum sterility assurance level of $10^{-6}$ in the number of microorganisms per container. A sterility assurance level of $10^{-6}$ is the probability of having 1 non-sterile package out of one million packages.

The "$D_{value}$" is the amount of energy required to kill 90% of the organisms present. For steam sterilization, the $D_{value}$ is the time required at a given temperature to reduce the number of viable cells or spores of a given microorganism to 10% of the initial number, according to P. Singleton and D. Sainsbury in *Dictionary of Microbiology and Molecular Biology*, 1988, John Wiley & Sons, New York, N.Y., pg. 256. According to ANSI standards for gamma radiation, the $D_{value}$ is the radiation dose required to kill 90% of the organisms of a homogeneous microbial population, which is defined by assuming that the death of microbes follows first order kinetics. In the case of non-ionizing radiation, the $D_{value}$ will be the non-ionizing radiation dose required to kill 90% of the organisms of a homogeneous microbial population, which is defined by assuming that the death of microbes follows first order kinetics. The $D_{value}$ is calculated using the Stumbo-Murphy-Cochran Equation: $D_{value}=U/(\text{Log } N_0\text{-Log } N_u)$, where $N_0$ is the initial number of microorganisms in each replicate unit, $N_u$ is ln(n/r), where n is the total number of replicate units exposed to the sterilizing dose U, and r is the number of units exposed to dose U that test negative for growth. Using the $D_{value}$, the sterilizing dose can be calculated. For sterilization of a medical device such as a single-use contact lens, the requirement is for a sterility assurance level of $10^{-6}$. The total dose required to sterilize the product therefore equals $D_{value}$ (log $N_o$-log $N_u$).

The term "ultraviolet radiation" or "UV radiation" means radiation having a wavelength or wavelengths between from 160 to 400 nm. If a range is specified following the term "ultraviolet radiation" or "UV radiation", a narrower range of radiation is meant within the 160 to 400 nm range. Further, the range specified, unless otherwise stated, means radiation having a wavelength or wavelengths within the range.

The term "monochromatic ultraviolet radiation" or "monochromatic UV radiation" means radiation having a wavelength or wavelengths between from 160 to 400 nm, and the majority of the radiation is concentrated within a bandwidth of 3 nm. Preferably the wavelength or wavelengths of the majority of the radiation represent more than 70%, more preferably more than 90% of the total radiation of the monochromatic UV radiation. Preferably the majority of radiation is within a bandwidth of 2 nm, more preferably within 1 nm. If the term "monochromatic UV radiation" is followed by a single wavelength within parenthesis, that wavelength represents the majority wavelength of the radiation. If the term monochromatic UV radiation is followed by a range within parenthesis, then the majority wavelength is within the specified range and/or the total range of radiation is within the range specified. The preferred monochromatic UV radiation has the majority wavelength or wavelengths within about 220 to 320 nm, more preferably within 240 to 280 mm. Preferably the total monochromatic UV radiation is within the range from 220 to 320 nm, more preferably within from 240 to 280 nm. A wavelength or wavelengths within these ranges are the most preferred, because those wavelengths are the most effective at rendering a microorganism sterile. The more preferred wavelength ranges comprise 257 nm, and presently, the most preferred range has the majority of radiation at 257 nm.

Examples of monochromatic UV radiation sources that produce monochromatic UV radiation include lasers and excimer lasers and excimer lamps. Lasers can be gas, ion, excimer, metal vapor, semi-conductor, and solid state. The terms "laser", "lamps" and "monochromatic UV radiation source", unless otherwise indicated, may be used interchangably in this application. The monochromatic UV radiation source can be pulsed, or continuous. A continuous monochromatic uv radiation source is either one that continuously emits radiation or that pulses at a frequency greater than 15 Hz. The radiation geometry provided by the apparatus can be beam expanded, line focused or spot scanned. The only requirement is that every surface of the medical device receives a sterilizing dose of radiation. An expanded laser or excimer lamp which can treat the entire medical device in a single exposure is preferred. The preferred monochromatic uv radiation source is a continuous (CW) frequency doubled laser. Preferably the monochromatic uv radiation source is collimated and/or coherent.

Alternatively, the medical device may be scanned using a monochromatic UV radiation source. There are two preferred scanning methods. Firstly, the medical device may be scanned using a raster scan which uses spot focused radiation, and the radiation source, the radiation and/or the medical device can be moved in at least the x and y directions. Preferably the radiation and/or the medical device are moved in the x and y directions. More preferably the radiation is moved in at least one direction by mirrors. If the radiation is moved in one direction, e.g. the x direction, by mirrors the medical device can be moved in the other direction, e.g. the y direction, for example by a conveyor. Most preferably the radiation is moved in the x and y directions by mirrors. The radiation is preferably from at least one radiation source, preferably a continuous source. For the raster scan, the scanning in the y direction is preferably 0.8 to 1.2 Hz, and the scanning in the x direction is preferably at least 70 times faster than the scanning in the y direction or visa-versa. This is to avoid artificial harmonics in the exposure area, that is, lissajous curves. Preferably the scan frequency in the x direction is 84 to 100 scans/second. For a raster scan, it preferably scans between 20-200 scans/sec, more preferably 60 scans/sec, and each scan preferably overlaps between 25 to 75 percent, more preferably approximately 50 percent, of the prior scan width. The beam width of the laser is typically 0.8 mm to 2.5 mm, more preferably about 1.4 mm.

Secondly, the medical device can be scanned by using line focused radiation preferably having a radiation beam width which is wide enough to cover the medical device in the x direction, and then the medical device, the monochromatic UV radiation source, and/or the radiation can be moved in the y direction until the entire medical device is treated with a sterilizing dose of radiation. Preferably, either the radiation, preferably by using mirrors, or the medical device, for example by a conveyor, is moved in the y direction. A line focus can be made by using a cylindrical lens which focuses a column-shaped laser beam into a line; or an excimer lamp may be formed into a line source, or the radiation from an excimer lamp may be focused into a line by its reflector system, e.g. by a trough ellipse or other conical-shaped reflector.

To deliver the necessary dose of radiation, the medical device can be treated or exposed multiple times, in this embodiment in which the medical device is scanned by scanning it multiple times. Multiple scans can be accomplished by scanning over the same area of the medical device multiple times or scanning over the entire medical device once and then scanning over the entire medical device again and/or again. Depending on the embodiment, the radiation, radiation source or medical device can be moved to treat the medical device multiple times. Preferably, the radiation is moved using mirrors, and/or the medical device is moved into and through the target area/volume of the monochromatic uv radiation source, and then back through the target area/volume, for example by a movable conveyor. Alternatively other means to convey the medical device such as hooks, or pusher bars can be used to transport the medical device into and/or through the target area/volume. The conveyor means can be used to transport the medical device during exposure or simply to transport the medical device to the target area/volume of the monochromatic UV radiation source, and away from the monochromatic uv radiation source after treatment.

Examples of monochromatic uv radiation sources include those that produce monochromatic UV radiation at the desired wavelength(s), or those whose wavelength(s) are frequency doubled, tripled, quadrupled, or otherwise tuned (e.g. by using a doubling crystal (e.g. alpha or beta barium borate (BBO), lithium triborate (LBO), or cesium lithium borate (CLBO) or optical parametric oscillator (OPO)) to produce uv radiation. Examples of these sources include argon ion lasers, krypton ion lasers, metal vapor lasers, (such as copper vapor lasers), and solid state lasers, such as, neodymium yttrium aluminum garnet (Nd:YAG), neodymium yttrium aluminum flouride (Nd:YAF), neodymium yttrium aluminum phosphate (Nd:YAP), neodymium vanadate (Nd:YVO$_4$), neodymiom glass (Nd:Glass), and solid state lasers. Other sources of monochromatic UV radiation include gas discharge tubes filled with gas mixtures in a laser or an excimer lamp which produce excimers in an electric discharge. Examples of gas mixtures which produce excimers include krypton and chlorine (KrCl), krypton and fluorine (KrF), xenon and iodine (XeI), chlorine (Cl$_2$), xenon and bromine (XeBr), bromine (Br$_2$), xenon and chlorine (XeCl), xenon and fluorine (XeF) argon and chlorine (ArCl), and argon and fluorine (ArF). These monochromatic uv radiation sources can be pulsed or continuous sources. These are only examples, other monochromatic UV radiation sources can be used in this invention.

Examples of useful commercially available monochromatic UV radiation sources include lasers available from Lambda Physik. One useful pulsed laser is a Krypton-Floride (Kr-F) laser produced by Lambda Physik having an output at 248 nm. Examples of commercially available excimer lamps include Xenon-Iodide (XeI) from Quark Physics which produces radiation at 253 nm, Krypton-Fluoride (KrF) from Quark Physics which produces radiation at 248=n. Another useful laser is a solid state Coherent Verde diode laser at 532 nm, which can be frequency doubled to 266 nm using mbd-266 resident enhancement cavity.

The monochromatic UV radiation source may be used in conjunction with other structural and optical elements to direct the radiation at the target. The excimer lamp is preferably used in conjunction with a reflector or reflectors. Alternatively the excimer lamp can be used with a beam integrator lens. The laser can be used with a scanner, mirror, such as galvo mirrors and turning mirrors, beam expander, chopper, beam splitter, diffuser, or focusing optics, such as lenses which focus the laser radiation into a spot or a line, or combinations of the above list. The optics are used to provide the proper dose of radiation to the target. Further, a despeckler device such as a diffusing or oscillating surface may be used to remove or mitigate the intensity variations in the radiation from the monochromatic UV radiation source on the micron scale due to interference speckle. In one embodiment, e.g. an apparatus of this invention comprises a laser in a scanning apparatus consisting of at least two mirrors which move a spot-focused beam back and forth in the target area.

This invention can be used to sterilize medical devices. The configuration of the system used to sterilize the medical device depends on the transmissivity of the medical device to monochromatic UV radiation. If the medical device is transmissive to at least a portion of the monochromatic ultraviolet radiation (preferably from 240 to 280 nm), for example, preferably greater than 10%, more preferably more than 50%, most preferably more than 75%, then a single monochromatic UV radiation source can be used to sterilize the medical device as long as at least 50 mJ/cm$^2$, more preferably at least 100 mJ/cm$^2$, most preferably at least 200 mJ/cm$^2$ of UV radiation reaches all the microorganisms and/or all surfaces of the medical device to be sterilized. In addition, if the medical device is transmissive to at least a portion of the monochromatic ultraviolet radiation (preferably from 240 to 280 nm), for example, preferably greater than 10%, more preferably more than 50%, most preferably more than 75%, then a single monochromatic continuous UV radiation source can be used to sterilize the medical device as long as at least 100 mW/cm$^2$, more preferably at least 250 mW/cm$^2$, most preferably at least 500 mW/cm$^2$ of UV radiation reaches all the microorganisms and/or all surfaces of the medical device to be sterilized. If the medical device is not transmissive to monochromatic UV radiation (preferably from 240 to 280 nm) or is transmissive to such a small percentage of UV radiation, for example, less than 10%, then more than one monochromatic UV radiation source will most likely be necessary to sterilize the medical device, or the radiation produced by a single monochromatic UV radiation source will have to be split, e.g. by a beam splitter, and directed at the medical device from different directions. However, any configuration and any number of monochromatic UV radiation sources can be used as long as the minimum levels of energy specified herein reach all the microorganisms or all the surfaces of the medical device which are to be sterilized.

Additionally, multiple monochromatic radiation sources, where at least one is a monochromatic uv radiation source can be used together to accomplish sterilization. Two or more monochromatic uv radiation sources can be used together to provide the same or different amounts of energy of the same wavelengths of monochromatic uv radiation to the medical device, or they can provide the same or different amounts of energy at different wavelengths of monochromatic uv radiation. The different levels of energy may be necessary to provide to the medical device because of the shape or transparency of the medical device. The different wavelengths may provide increased levels of sterility, because different microorganisms that have to be sterilized on a medical device may have greater or lesser sensitivities to uv radiation at different wavelengths; therefore, multiple monochromatic uv radiation sources can be used which produce monochromatic uv radiation at different wavelengths which when used together will successfully sterilize all the microorganisms, that might not otherwise be sterilized, or would require greater levels of energy if only one monochromatic uv radiation source is used.

Alternatively, a monochromatic uv radiation source of this invention can be used in combination with one or more monochromatic radiation sources within the visible or infrared radiation spectra. Some microorganisms have an action spectrum with peaks outside the uv region. For these microorganisms a combination of sources one of which is a source which produces radiation outside of the uv region and the other a monochromatic uv radiation source will provide sterilization. For example, vegetative microorganisms and sporolated fungi with dark spore coats are more easily sterilized and at lower levels of radiation using combinations of monochromatic sources producing radiation within the uv and visible ranges, and uv and infrared ranges. Another benefit of using more than one monochromatic radiation source wherein at least one is a monochromatic uv radiation source at particularly effective wavelength is that that same wavelength may cause damage to the package or the medical device and therefore cannot be used at the levels of energy necessary to achieve sterility; however, in combination with another monochromatic radiation source is effective to achieve sterility.

This invention is preferably used to sterilize medical devices which are in sealed containers. If the medical device is to be sterilized after placing it in its container, the container must be at least partially transmissive to at least a portion of the monochromatic ultraviolet radiation (preferably at the majority of the radiation), preferably the container is transmissive to at least 25% of the monochromatic ultraviolet radiation (preferably at the majority of the radiation), more preferably the container is transmissive to at least 50% of the monochromatic ultraviolet radiation (preferably at the majority of the radiation), and most preferably the container is transmissive to at least 75% of the monochromatic ultraviolet radiation (preferably at the majority of the radiation). Ideally, the container is transmissive to substantially all of the monochromatic ultraviolet radiation. If the medical device is transmissive to at least a portion of the monochromatic ultraviolet radiation (preferably at the majority of the radiation), and a monochromatic UV radiation source is used to sterilize the medical device, and if the medical device is in a container, then the container can be transmissive to at least a portion of UV radiation only in one area of the container, as long as enough radiation can reach all the microorganisms and all of the surfaces of the medical device and contents of the container. (The contents of the container include the inside surfaces of the container and any solution or other storage medium for the medical device which is inside the container). However, if more than one monochromatic UV radiation source is used, it is preferred that the container is at least partially transmissive to monochromatic ultraviolet radiation at least at the majority of the radiation over most of the surface area of the container, and preferably substantially over the entire surface area, that is, that the container, at the time of exposure to the sterilizing radiation, preferably does not comprise any materials that have less than 10%, more preferably not less than 25% monochromatic ultraviolet radiation transmissivity at the majority of the radiation. More preferably, the container is transmissive in substantially all directions to at least 50% of the monochromatic UV radiation (preferably at the majority of the radiation), and most preferably the container is transmissive in substantially all directions to at least 75% of the monochromatic UV radiation (preferably at the majority of the radiation). Ideally, the container is transmissive in substantially all directions to substantially all of the monochromatic UV radiation.

Examples of medical devices which may be used in the process of this invention include, for example, catheters, surgical equipment, implants, stents, sutures, packing, staples, and bandages, and the like. Materials which may be used to make the medical devices include metals, glycerol monomethythacrylate, polyvinylalcohol, polyvinypyrrolidone, 2-hydroxyethyl methacrylate (HEMA), methacryloxypropyltris (trimethylsiloxy)silane, polydimethylsiloxane, methylacrylic acid, methylmethacrylate, urethanes, polypropylene, polylactide, polyglactide, polyethylene glycol, polypropylene glycol, and the like, and the materials described below.

To decrease the complexity and energy demands of this method of sterilization, it would follow that it would be preferred that the medical device is at least partially transmissive to monochromatic ultraviolet radiation (preferably at the majority wavelength), preferably the medical device is transmissive to at least 10% of the monochromatic ultraviolet radiation (preferably at the majority wavelength), more preferably the medical device is transmissive to at least 25% of the monochromatic ultraviolet radiation (preferably at the majority wavelength), and most preferably the medical device is transmissive to at least 50% of the monochromatic ultraviolet radiation (preferably at the majority wavelength). The preferred medical device treated by the method of this invention is a contact lens. It is more preferred that the contact lens is in a hermetically sealed contact lens container, and even more preferred that the contact lens container holds a liquid in which the contact lens is immersed. Even though the method would be simplified by using a UV transmissive medical device, the presently preferred contact lens is a contact lens comprising a UV-blocker which blocks greater than 30%, more preferably greater than 50%, and most preferably greater than 80% of the UV radiation (200-400 nm) impinging upon it. The preferred embodiment, the process of sterilizing a contact lens, will be described herein; however, it is apparent that other medical devices, such as those listed above, can be substituted for the contact lenses in the method described in detail below for contact lenses.

It is preferred that the process of this invention is incorporated into an in-line continuous contact lens manufacturing and packaging process. In the most preferred embodiment, the contact lens is formed and placed in a contact lens container, solution is added to the container, the container is sealed and the container is subjected to short duration, high intensity radiation from a monochromatic UV radiation source, preferably a laser producing a majority of the radiation at 257 nm, either by scanning or pulsing, to produce a sterile packaged contact lens which is ready for distribution and use. In the preferred embodiment, the contact lens comprises a hydrogel material and the contact lens is stored in an aqueous solution in the container. The manufacture and placement of the contact lens in the container can be by any process for making contact lenses including those described in, for example, U.S. Pat. Nos. 5,435,943; 5,395,558; 5,039, 459; 4,889,664; 4,565,348; 4,495,313, incorporated herein by reference. Other methods of manufacturing contact lenses are disclosed in other patents, and are known to a person of ordinary skill in the art.

The preferred method provides that a contact lens mold is formed by injection molding two thermoplastic contact lens mold halves which, when put together, form a cavity in the shape of the contact lens. These thermoplastic contact lens molds are typically used once to form a contact lens. Reusable lens molds made out of more durable materials, for example, glass or metal can also be used. Typically, before the lens molds are put together, the monomer or prepolymer mixture which forms the contact lens polymer is injected into a first mold half and a second mold half is placed onto the first mold half which pushes out any excess monomer or prepolymer mixture. However, a one-piece mold can be used to form the contact lens, or the monomer or prepolymer mixture can be injected between the molds after assembly of the molds. The monomer or prepolymer mixture is then cured to form the contact lens. Curing of the monomer or prepolymer mixture is preferably initiated by using photoinitiation. After curing the monomer or prepolymer mixture, the mold halves are removed, and the contact lens is hydrated, is if needed. After hydration, preferably one contact lens is placed in a contact lens container. It is preferred that each contact lens container also contains at least enough aqueous solution to fully wet the contact lens in the container, but the presence of aqueous solution is not required in the process of this invention. The aqueous solution, if present, can be added to the container before or after placing the contact lens in the container. Further, the container can be sealed before or after the sterilization step. Alternatively, the container can be sealed before and after the sterilization step if multiple layers of the container are added in multiple steps. For example, a sealed container can be shrink-wrapped or a label added after the sterilization step; or there can be multiple sterilization steps before and after sealing the container. For example, the container can undergo the sterilization step while empty, and/or when it has liquid in it and/or when it has a contact lens placed in it and is not sealed, and/or after the container is sealed with the contact lens and optional liquid present in the container. In additional embodiments, the individual parts and contents of the container can be individually treated by the method of this invention, and then assembled, and/or treated again. It is presently preferred to hermetically seal the container in which a contact lens is present prior to the process of sterilization, and to perform the step of subjecting the hermetically sealed container having the contact lens therein to UV radiation (preferably 257 nm) only once. The container can be sealed by any means which provides a hermetically sealed container.

The contact lenses useful in accordance with the present invention may be formed from any materials useful for contact lenses. For example, the lenses may be hydrophilic lenses formed from the polymerization or copolymerization of acrylates or methacrylates, such as 2-hydroxyethyl methacrylate (i.e., HEMA); hydrophobic lenses formed from polysiloxanes; or lenses formed from copolymers displaying a range of hydrophobic and hydrophilic properties. The preferred contact lens material is Etafilcon-A which comprises HEMA, MAA, EGDMA, TGDMA, and Darocur. Useful contact lens materials are described in U.S. Pat. Nos. 5,484,863; 5,039, 459; 4,889,664; 5,0684,058; 5,654,350; 5,648,402; 5,311, 223; 5,304,584; 5,256,751; 5,196,458; 4,495,313; and 4,680, 336, incorporated herein by reference.

Additionally, the process of this invention can be used to sterilize contact lenses which contain ultraviolet radiation blocking agents. Contact lenses containing monochromatic ultraviolet radiation blocking agents include, Acuvue® and Surevue® made by Johnson & Johnson Vision Products. Blocking agents which can be used in contact lens compositions include Norbloc™ 7966, which is 2-(2'-hydroxy-5-methacryloxyethylphenyl)-2H-benzotriazole; other benzotriazoles, such as, 2-(2'-hydroxy-5'methacrylyloxyethylphenyl)-2H-benzotriazole; 2-{3'-tert-butyl-2'-hydroxy-5'-(3"methacryloyloxypropyl)phenyl}-5-chlorobenzotriazole; and benzophenones, such as, 1,3-bis(4-benzoyl-3-hydroxyphenoxy)-2-propyl)(meth)acrylate; 2-hydroxy-4-((meth)acryloxyethoxy)benzophenone; 4-methacryloxy-2-hydroxybenzophenone, others disclosed in U.S. Pat. Nos. 5,133,745; 4,528,311; 4,716,234; 4,528,311 and 5,681,871, and others known to a person of ordinary skill in the art. Contact lenses can be made according to the examples and teachings in U.S. Pat. Nos. 5,133,745; 4,716, 234; 4,528,311; 4,304,895 and 5,681,871. Also the process of this invention can be used to sterilize contact lenses which contain tints, including visibility tints, including Reactive Blue #4 (2-anthracenesulfonic acid, 1-amino-4-(3-((4,6-dichloro-s-triazin-2-YL)amino)-4-sulfoanilino)9,10-dihydro-9,10-dioxo-) and other materials disclosed in U.S. Pat. No. 5,292,350. The most preferred lens material is Etafilcon-A further comprising Norbloc™ and Reactive Blue #4.

The aqueous solution, if present in the contact lens container, is preferably buffered to a pH of between about 6.5 to about 7.8 in order to approximate the pH of the fluids in the eye. The solution may be buffered by a wide variety of buffers including phosphates, borates, citrates, and other biocompatible buffers known to a person of ordinary skill in the art. The presently preferred buffer is a borate solution. The amount of solution depends on the size of the container. The solution preferably does not contain any preservatives. Typically, the container has a volume between 0.5 milliliters and 50 milliliters, preferably about 1 milliliter, and there is between 0.1 milliliter to 1 milliliters, preferably about 0.5 milliliters of solution in the container.

Containers which are useful in this invention are any of the known containers which are or can be hermetically sealed as long as the containers are at least partially transmissive to monochromatic ultraviolet radiation (preferably from 240 to 280 nm). The containers can be UV transmissive glass, thermoplastic pouches and bags, cyclic olefin copolymers, injection molded or thermoformed plastic containers, and conventional bowls and lids for contact lenses, as long as enough monochromatic ultraviolet radiation (preferably from 240 to 280 nm) can penetrate the container to sterilize the contents of the container. It is presently preferred that the contact lens container comprises a bowl and a lid. It is preferred that the material or materials of at least the bowl of the container are at least partially transmissive to monochromatic ultraviolet radiation. Particularly, for the sterilization of a contact lens comprising UV-blocker, it is even more preferred that the bowl and the lid are at least partially transmissive to monochromatic ultraviolet radiation, preferably in all directions. To accomplish this, it is preferred to replace the conventional foil lid with a thermoplastic lid, which may consist of one or more layers of, for example, Aclar, nylon, polyamide, polyvinylidenefluorides (PVDF), polyvinylchlorides (PVC), Saran (polyvinylidene chloride (PVDC)), Saran coated PVC, polyfluorides, e.g. polytetrafluorethylene, cast polypropylene, acrylics, polyethylenes, polystyrenes, and polychlorofluorides e.g. polychlorotrifluoroethylene, polyesters, and copolymers of these materials and cyclic olefin copolymers. It is presently preferred that the bowl is a polyolefin, and the lid comprises polypropylene. The materials of the bowl and the lidstock should preferably be free of any component that will scatter light. The most preferred method of sealing the container is to heat seal the thermoplastic lid to the thermoplastic bowl. The most preferred containers and materials for the container are described in James Peck, et al, U.S. Ser. No. 09/259,795, titled, "Package for Medical Device" (VTN-445) filed Mar. 1, 1999 which is incorporated herein by reference.

Sterilization of the contact lens and preferably the contents of the container is achieved by subjecting the container to high intensity radiation, preferably in a short duration, comprising monochromatic ultraviolet radiation (preferably from 240 to 280 nm) from a monochromatic UV radiation source, wherein the energy density of said high intensity monochromatic ultraviolet radiation (preferably from 240 to 280 nm) inside said container is sufficient to provide complete inactivation of the respective microorganisms. The radiation preferably comprises UV radiation in the range 240-320 nm, because it has been determined that radiation at these wavelengths is most responsible for the inactivation of microorganisms. Different microorganisms are known to be affected differently by monochromatic ultraviolet radiation (at the specific individual wavelengths between about 240 and 280 nm). Viruses are susceptible to UV radiation, and vegetative bacteria are more susceptible to UV radiation. The spore-forming microorganisms are known to be the most resistant to UV radiation. The reasons for the resistance of the spores to UV radiation is primarily attributed to the composition of the outer coat of the spore and the ability of spores to refract light. We have determined that one of the most resistant microorganism to this method of sterilization is *Bacillus stearothermophilus* (ATCC 7953). The $D_{value}$ for *Bacillus stearothermophilus* (ATCC 7953) is at least 23.7 mJ/cm² monochromatic ultraviolet radiation (257 nm) to the spores. The Dvalue was determined using an apparatus having a continuous, scanning frequency doubled Ar ion laser producing radiation at 257 nm (2 W) Coherent Innova® Sabre®, FreD™, which will be described in greater detail below. For a sterility assurance level of $10^{-3}$, using the Dvalue 23.7 mJ/cm², the dose to the microorganisms (where the initial inoculum is 104 cfu/container) is at least 166 mJ/cm² of UV radiation (257 mm). For a sterility assurance level of $10^{-6}$, the dose to the microorganisms is at least 237 mJ/cm² of UV radiation (257 nm). For a sterility assurance level of $10^{-9}$, the dose to the microorganisms is at least 308 mJ/cm² of UV radiation (257 nm). For a sterility assurance level of $10^{-12}$, the dose to the microorganisms is at least 379 mJ/cm² of UV radiation (257 nm). For an initial inoculum of 106, the microorganisms are exposed to at least 284 mJ/cm² of said UV radiation (257 nm) to provide a sterility assurance level of $10^{-6}$. In the preferred embodiment, in which the medical device is a UV-blocker lens in a container having approximately 50% transmissivity for UV radiation (257 nm), the energy is provided by two lasers each of which provides at least 284 mJ/cm² UV radiation (257 nm) to the container, and the lasers irradiate both sides simultaneously, whereby the contact lens, and more preferably the contact lens and the contents of the container are rendered sterile. The container permits approximately 50% of the UV radiation impinging on it from each laser to reach the contents of the container. The amounts of energy, and $D_{values}$ required for sterility may vary depending upon the wavelength(s) provided by the monochromatic uv radiation source(s), and the delivery mechanism of the radiation, and the medical device to be sterilized.

As described above, the high intensity monochromatic ultraviolet radiation can be generated and directed to the container by one or more monochromatic UV radiation sources, e.g. lasers or excimer lasers or lamps, with or without reflectors, lightguides, lightpipes, fiber optics, dioptric or catadioptric optical systems to focus light on the product. It is preferred that at least 75% or more of the total energy which reaches all the surfaces of the medical device to be sterilized is ultraviolet radiation (preferably from 240 to 280 nm). For a medical device in a container, it is preferred that at least 75% or more of the total energy which reaches all the surfaces of the medical device, and the contents of the container is UV radiation (preferably from 240 to 280 nm). For many polymers which are commonly used for contact lens containers and contact lenses, which were described earlier, radiation at wavelengths less than 240 nm is absorbed by the polymers and may cause chain scissions within the polymers. Since the laser emits at a single wavelength or a narrow range of wavelengths, a source which produces radiation below 240 nm can be avoided which is a benefit over broad band radiation sources.

Sterilization of the container, which preferably comprises at least one contact lens and aqueous solution is preferably achieved by subjecting the contact lens and container to short duration, high intensity monochromatic ultraviolet radiation, wherein the energy density of said high intensity monochromatic ultraviolet radiation 257 nm at all the surfaces of the contact lens is at least 166 mJ/cm², more preferably at least 237 mJ/cm², most preferably at least 284 mJ/cm², whereby the contact lens, and more preferably the contact lens and the contents of the container are rendered sterile.

In the preferred embodiment, the monochromatic ultraviolet radiation is delivered to the medical device by a laser system which exposes the entire medical device simultaneously or scans the medical device. The medical device can be scanned via a line laser or raster scan with a narrow spectrum of radiation (e.g. 257 nm). The exposures or scans are short and intense, that is, the exposures or scans last less than 5 seconds, more preferably less than 3 seconds, and most preferably less than 1 second. In the preferred system each exposure of the entire medical device lasts less than 0.5 second, more preferably less than 0.1 second, most preferably about 1 millisecond, and the time between exposures of the medical device, if more than one exposure is necessary to achieve sterility is about 100 to about 200 milliseconds; therefore, the sterilization process can be completed within a few seconds even if it takes multiple exposures to deliver the sterilizing dose. The pulses or exposures deliver enough energy to sterilize the medical device and contents of the container. Each exposure of energy in this system delivers a large amount of energy to surfaces of the contact lens and the container in a short period of time. It is preferred that at least 284 mJ/cm² (257 nm) reaches the surface of the contact lens in less than 10 milliseconds, more preferably in less than 1 millisecond, most preferably in less than 500 microseconds. More preferably, at least 1 J/cm² reaches the microorganisms in less than 1 millisecond. It has been found that the effectiveness of the system at sterilizing is dependent not only on the total amount of energy that is supplied to the container, but that there is a maximum amount of time (and exposures) in which that energy needs to be delivered to the container. It has been determined that the energy required to render the contact lens sterile is preferably delivered to the surface of the contact lens in at most three exposures, more preferably at most two exposures and most preferably in one exposure of radiation from at least one source in a pulsed or scanning UV radiation system. It is preferred that the monochromatic uv radiation source in the preferred embodiment provides at least 284 mJ/cm², more preferably at least 568 mJ/cm², and most preferably at least 1.2 J/cm² UV radiation (257 nm) in each exposure to the microorganisms. It is also preferred that the laser in the preferred embodiment produces at least 568 mJ/cm², more preferably at least 1.2 J/cm² and most preferably at least 2.4 J/cm² UV radiation (257 nm). It is preferably with a minimum of 568 mJ/cm² delivered in each exposure. For a medical device in a container, the medical device having less than 20% transmissivity (257 nm), it is preferred that multiple monochromatic uv radiation sources are used simultaneously to produce at least 900 mJ/cm² total UV radiation (257 nm) per exposure, more preferably at least 1.2 J/cm² total UV radiation (257 nm) per exposure, and most preferably at least 2.4 J/cm² total UV radiation (257 nm) per exposure of the container.

The application of the short duration, high intensity monochromatic ultraviolet radiation can be accomplished by using one or more lasers. In the preferred embodiment, if one laser is used it is preferably directed at the contact lens at the base, preferably the bowl, of the container. If two sources of radiation are used, or the radiation from a single source is split into two, preferably one is directed at the contact lens through the base and the other is directed at the top, preferably through the lid of the container. As long as the contents of the container receives a sterilizing dose of radiation, and each single cell of microorganism is exposed to sufficient energy to inactivate it, the configuration of the sources of the radiation is not important. Only one laser is necessary when the container and medical device have sufficient transmissivity to allow sufficient energy to transmit through the container and device to affect sterility on the entire contents of the container. For example, one laser may be effective for a container holding a contact lens which does not have a UV-blocker in its polymer, or a contact lens that is transmissive to greater than 30%, more preferably greater than 50% of UV radiation (257 nm).

The presently preferred apparatus for delivering the high intensity radiation to the contact lens having a UV-blocker in a container with an aqueous solution in the container is a frequency-doubled Argon ion continuous wave (CW) laser from Coherent Laser (Santa Clara Calif.) which emits greater than 1 watt at 257 nm, and is capable of delivering 150 mJ/cm² to the outside of the container. The preferred system is shown in FIG. 1. FIG. 1 shows two laser assemblies 21 and 31. Laser assembly 21 comprises laser 22, frequency doubler 23, turning mirrors 24 and 25, scanner 26 comprising mirrors 27 and 28. Laser assembly 31 comprises laser 32, frequency doubler 33, turning mirrors 34 and 35, scanner 36 having two mirrors 37 and 38. Also shown in FIG. 1 is the chamber 40. The chamber comprises a motion-controlled stage 47 to move the product within and through the treatment area on the product support 49. The laser assemblies 21 and 31 face each other with a space between them for the product support 49 holding the container or containers to be sterilized. The system is shown with one container 50 on the product support 49 ready for sterilization. The laser assemblies 21 and 31 scan the container 50 simultaneously. Lines A and B show the radiation's path to the container 50. Each laser assembly 21 and 31 generates a minimum of 284 mJ/cm² of UV radiation (257 nm), more preferably a minimum of 568 mJ/cm² (257 nm) per exposure. The chamber 40 is preferably light-tight when the product is scanned, and more preferably the chamber 40 and laser assemblies 21 and 31 are configured such that all are light-tight, and the junctions 51 and 52 between them allow the radiation A and B to pass to the container 50, but not outside of the chamber 40 or assemblies 21 and 31. The container 40, comprises a contact lens and aqueous solution (not shown). Preferably, only when a light-tight chamber is established will the shutter on the laser be opened. It is believed that a light-tight chamber will prevent any photo-annealing of the microorganisms' damaged DNA after subjecting the medical device to UV radiation (preferably from 240 to 280 nm).

The containers are preferably placed between the two lasers so that the contact lenses are closest to the center-line between the radiation from the two lasers. The product support 29 can consist of any materials which will hold the containers and permit enough monochromatic ultraviolet radiation (257 nm) to reach the contents of the one or more containers. For example, it can comprise polymeric or other glass materials in any configuration which holds the containers, e.g. sheet, mesh, or bars. It is presently preferred that the product support comprises quartz.

Figure 2:
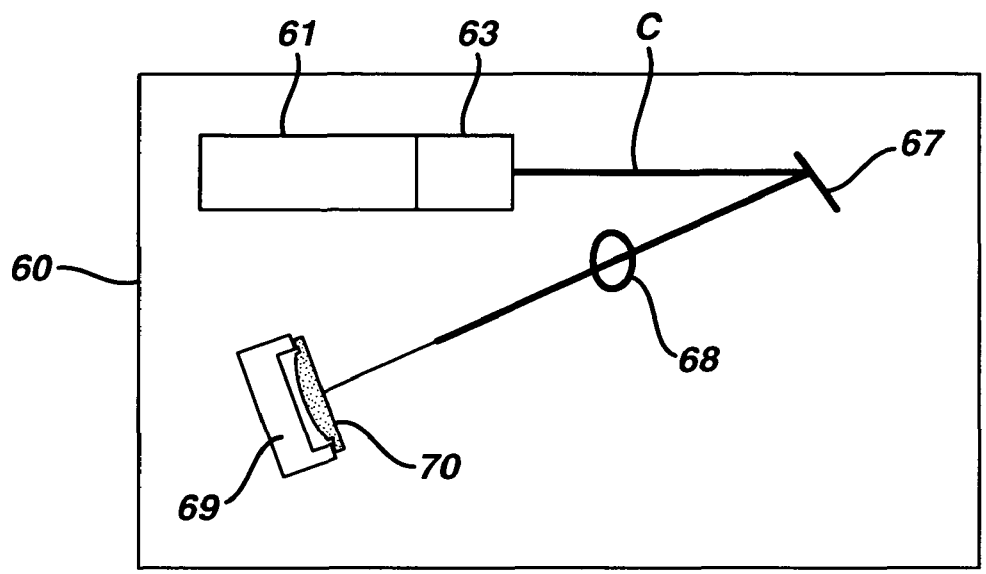
FIG. 2 illustrates a second embodiment of an apparatus of this invention.

FIG. 2 illustrates a second embodiment of the invention which shows a treatment chamber 60 which comprises laser 61, frequency doubler 63, galvo mirror 67, spherical lens 68, and product support 69. The laser radiation beam 62 is shown exiting the laser, deflected by the galvo mirror 67 and focused by spherical lens 68 onto a container 70 shown in the product support 69. The galvo mirror 67 is used to raster scan the container 70 in both the x and y directions. The spherical lens 68 focuses the beam width down to a smaller point which increases the intensity of the radiation at that point.

Figure 3:
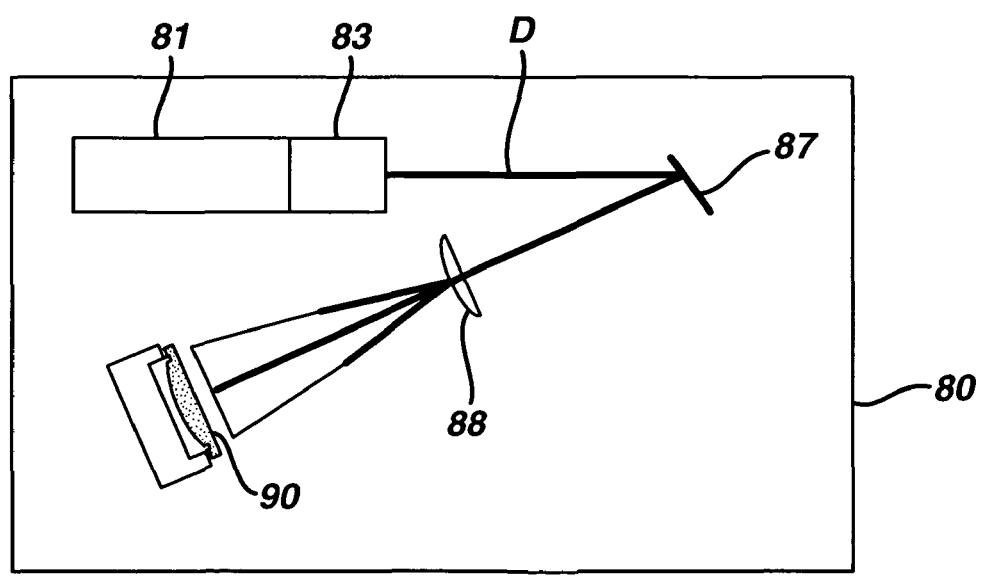
FIG. 3 illustrates a third embodiment of an apparatus of this invention.

FIG. 3 illustrates a third embodiment of this invention, which shows a treatment chamber 80 which comprises laser 81, frequency doubler 83, galvo mirror 87, cylindrical lens 88, and product support 89. The laser radiation beam 82 is shown exiting the laser, deflected by the galvo mirror 87 and focused by cylindrical lens 88 onto a container 90 shown in the product support 89. The cylindrical lens 88 focuses the radiation beam D into a line in the x-direction having a width (or length) greater than the container 90. The galvo mirror 87 is used to scan the container 90 with the line of radiation in the y-direction.

The energy levels specified herein can be used to determine the exposure that is required to sterilize a medical device in a container. The transmissivity of a container and the medical device within the container must be determined. As taught herein, it is now known that the minimum level of energy which must reach the inside of the container and the surface of the medical device to obtain sterilization must be equivalent to at least 450 mJ/cm² of UV radiation at 257 nm. The following formula can be used to calculate the amount of energy that must be provided from the one or more monochromatic uv radiation sources to achieve sterility. The following formula is suited for a system which has two monochromatic uv radiation sources, but can be modified if one or more than two monochromatic uv radiation sources are used:

Total energy from all monochromatic uv radiation sources $E=E_a+E_b$, where $E_a$ is the energy above the contact lens in the container, and $E_b$ is the energy below the contact lens in the container.

where $E_a = E_U[e^{-k_{LS}x_{LS}}] + E_L[e^{-k_B x_B}][e^{-k_L x_L}]$,
and $E_b = E_U[e^{-k_{LS}x_{LS}}][e^{-k_L x_L}] + E_L[e^{-k_B x_B}]$ where transmissivity T=I (intensity which penetrates a material)/$I_0$ (intensity incident on a material)=$e^{-kx}$ where k is the transmissivity constant of a material at 257 nm and x is the thickness of the material. $E_U$ is the energy from a monochromatic uv radiation source located above the container. $E_L$ is the energy from a monochromatic uv radiation source located below the container. The subscript LS indicates lidstock. The subscript L indicates lens. The subscript B indicates bowl. $E_a$ and $E_b$ each have to be at least 3.6 J/cm$^2$ UV radiation (257 nm) to achieve sterilization of the medical device at an SAL of $10^{-12}$ If the transmissivity of the container or medical device is increased or decreased, the energy of the lasers can be calculated, because $E_a$ and $E_b$ are known. (For the preferred embodiment herein, the contribution of the UV radiation (257 nm) which passes through the UV-blocking contact lens was assumed to be zero when determining the amount of UV radiation which the microorganism is subjected to on each side of the lens.)

Initially, a prototype system consisting of one laser using mirrors to raster scan the package, like the one shown in FIG. 2, was evaluated for sterilization. The laser was capable of delivering 150 mJ/cm$^2$ to the outside of the container. The laser was a frequency-doubled Argon ion continuous wave (CW) laser from Coherent Laser (CA) which emitted 1 watt at 257 nm. The system had a spherical mirror which focused the beam. The beam had an area of 0.7 m$^2$. The raster scan in the x direction was 90 Hz for 23 mm and the y direction was 1 Hz for 23 mm which covered the portion of the contact lens container where the contact lens and the solution was stored. The overlap area in consecutive scans was 0.35 mm.

Microbiological evaluation of the effectiveness of the system was conducted using containers, consisting of bowls and lidstock, (both about 50% transmissible to UV radiation (257 nm)), holding UV-blocking contact lenses (20% transmissive to 257 nm) in a non-preserved solution of buffered borate. The test microorganism was added at a concentration of 10$^4$ colony forming unit/package (cfu/pkg). The closed intact containers were exposed to the laser and subjected to 100 mJ/cm$^2$ (257 nm) from the laser. One hundred containers containing Bacillus stearothermophilus (ATCC 7953) or Aspergillus niger (ATCC 16404) spores were each exposed to a total of 100 mJ/cm$^2$ UV radiation (257 nm). The containers inoculated with Bacillus stearothermophilus (ATCC 7953) were then processed in a laminar flow hood whereby the entire contents of the container were placed into potato dextrose broth and incubated at 25° C. for 14 days. The containers inoculated with Aspergillus niger (ATCC 16404) spore preparations were transferred to tubes containing 40 ml of trypticase soy broth and incubated for 14-days at 35-37° C. This tube terminal sterilization method allows for the detection of the viability of 1-single cell. After 14-days of incubation, the tubes were visually evaluated for turbidity and designated as positive for growth or negative for no growth. The positive tubes were subsequently identified and confirmed as the microorganism inoculated in the test. This experiment was repeated with 100 additional tubes for 150 mJ/cm$^2$ exposure at 257 nm, and repeated again for 450 mJ/cm$^2$ cumulative exposure at 257 nm. The number of test tubes with viable test microorganisms out of the one hundred tested at each energy level were recorded in Table 1.

The results in Table 1 clearly show that the amount of energy produced by the system was capable of inactivating some of the test microorganisms; however, it was not effective in inactivating any of the more resistant spore formers. However, this system could be used to deliver enough energy in one exposure to sterilize a non-UV-blocking contact lens in an aqueous solution in a container having transmissivity greater than 50% for 257 nm radiation.

TABLE 1

| | Number of positive tubes/100 | | |
|---|---|---|---|
| Microorganism | 100 mJ/cm$^2$ | 150 mj/cm$^2$ | 450 mj/cm$^2$ |
| Bacillus stearothermophilus (ATCC 7953) | 31 | 25 | 9 |
| Aspergillus niger (ATCC 16404) | 100 | 100 | 100 |

Terminal sterilization was not achieved for Aspergillus niger for this set of conditions. The Dvalue for Aspergillus niger was determined from plate counts as follows:

6 random samples of each organism and condition were plated and processed as described below. Samples were serially diluted into duplicate pour plates using standard plate count method were prepared from each dilution to a level of countable plates between 20-300 cfu. Bacillus stearothermophilus was diluted serially and added to petri dishes followed by pouring tempered Trypticase Soy Agar. The agar was allowed to solidify and then the plates were inverted and incubated at 55-60 degrees C. for a maximum of 3 days. Aspergillus niger was serially diluted and added to petri dishes followed by pouring tempered Potato Dextrose Agar. The agar was allowed to solidify and then the plates of Aspergillus niger were inverted and incubated at 25-30 degrees C. for a maximum of 3 days.

After incubation, each plate was enumerated and the total counts for the total number of bacteria remaining in each package were determined.

100 package samples of each organism were exposed to each of the conditions outlined above. These samples were processed by placing the treated contents of the blister package into 40 ml volumes of Trypticase Soy Broth (B. stearo.) or Potato Dextrose Broth (A. niger) and incubating at stated temperatures for a period of 14 days.

Initial concentrations of each organism were:
 B. stearo.=1.02×10$^6$ spores/blister
 A. niger=5.20×10$^5$ spores/blister The number of survivors for each microorganism for each of the treatment conditions for the plate counts method are shown in Table 2.

TABLE 2

| Number of colony forming units for each treatment. | | | |
|---|---|---|---|
| Dose (mj/cm$^2$) | Scans | Bacillus stearothermophilus (ATCC 7953) | Aspergillus niger (ATCC 16404) |
| 0 | 0 | 258000 | 53333 |
| 50 | 1 | 3 | 2858 |
| 100 | 1 | 1 | 842 |
| 100 | 3 | 0 | 2475 |

TABLE 2-continued

Number of colony forming units for each treatment.

| Dose (mj/cm²) | Scans | Bacillus stearothermophilus (ATCC 7953) | Aspergillus niger (ATCC 16404) |
|---|---|---|---|
| 150 | 1 | 0 | 933 |
| 150 | 3 | 0 | 2225 |
| 450 | 3 | 0 | 850 |

Dvalues were determine from the slope of the log of survivors and treatment dose. The Dvalue is the energy required for a one log reduction. These data are shown in FIG. 4 and FIG. 5.

Although not preferred modes of this invention, it has been determined that this method of sterilization can be enhanced by adding chemicals, bactericides, surfactants, preservatives or heat to the contents of the container. Also the method of sterilization can be enhanced by shaking the container, or exposing the container to sonic vibration energy as it is exposed or between exposures to the laser or by heating the container. These additional methods may be required to decrease the Dvalue of *Aspergillus niger* which from the data above was at least 188 mJ/cm².

This invention has been described with reference to particular embodiments; however, variations within the scope of the following claims are apparent to those of ordinary skill in the art.

We claim:

1. A process of sterilizing a contact lens immersed in an aqueous liquid against *Bacillus stearotheromophilus* (ATCC 7953) to a sterility assurance level of at least $10^{-9}$, wherein said contact lens and said aqueous liquid are hermetically sealed in a container consisting of the step of
   penetrating said hermetically sealed container containing a contact lens immersed in an aqueous liquid with at least 284 mJ/cm² in the range of 240-280 nm of UV radiation from a monochromatic UV radiation source.

2. The process of claim 1 wherein, said contact lens is exposed to at least 308 mJ/cm² of said UV radiation of 257 nm during said penetrating step.

3. The process of claim 1 wherein said monochromatic UV radiation source is at least one laser.

4. The process of claim 1 wherein said penetrating step is accomplished by a line-focused laser scanning said hermetically sealed container.

5. The process of claim 1 wherein said penetrating step is accomplished by pulsing said hermetically sealed container.

6. The process of claim 1 wherein said monochromatic UV radiation source further comprises at least one of the following group: reflector, beam integrator lens, scanner, mirror, beam expander, chopper, beam splitter, diffuser, focusing optics, and a despeckler.

7. The process of claim 1 wherein said contact lens is transmissive to at least 25% of the monochromatic UV radiation.

8. The process of claim 1, wherein said radiation is delivered by more than 1 monochromatic UV radiation sources simultaneously.

9. The process of claim 1, wherein said radiation is delivered by more than 1 monochromatic UV radiation sources, said monochromatic UV radiation source producing differing wavelengths.

10. The process of claim 1 wherein said container is transmissive to at least 50% of said monochromatic ultraviolet radiation at 257 nm.

11. The process of claim 1, further wherein said container is transmissive to at least 50% of said radiation at 257 nm in substantially all directions.

12. The process of claim 1 wherein said container comprises a lid and a bowl, wherein said lid and said bowl comprise thermoplastics and said lid and said bowl are transmissive to at least 50% of said radiation at 257 nm in substantially all directions.

13. The process of claim 1 wherein said medical device is a contact lens, and wherein said subjecting step follows the steps of:
   (a) forming a contact lens;
   (b) placing said contact lens in a container; and
   (c) moving said container into an apparatus comprising a radiation source;
   and wherein said apparatus is light-tight during said subjecting step.

14. The process of claim 13 wherein said medical device comprises a contact lens comprising UV-blocker which blocks greater than 50% of the radiation between 257 nm.

15. The method of claim 1 wherein the process is performed as a step of an in-line continuous contact lens manufacturing and packaging process.

* * * * *